United States Patent [19]

Damico et al.

[11] Patent Number: 4,886,512
[45] Date of Patent: Dec. 12, 1989

[54] INCONTINENT GARMENT WITH ELASTICIZED POUCH

[75] Inventors: Joyce A. Damico; Rebecca J. Weber, both of Neenah, Wis.

[73] Assignee: Kimberly-Clark Corporation, Neenah, Wis.

[21] Appl. No.: 481,593

[22] Filed: Apr. 4, 1983

[51] Int. Cl.[4] .......................... A61F 13/16; A41B 9/12
[52] U.S. Cl. ................................................... 609/385.2
[58] Field of Search ....................................... 604/385

[56] References Cited

U.S. PATENT DOCUMENTS

| 2,273,542 | 2/1942 | Tasker . |
| 2,965,102 | 12/1960 | Harwood . |
| 3,371,668 | 3/1968 | Johnson . |
| 4,050,462 | 9/1977 | Woon et al. . |
| 4,182,334 | 1/1980 | Johnson . |
| 4,226,238 | 10/1980 | Bianco . |
| 4,253,461 | 3/1981 | Strickland et al. . |
| 4,315,508 | 2/1982 | Bolick . |
| 4,324,245 | 4/1982 | Mesek et al. . |
| 4,333,782 | 6/1982 | Pieniak . |
| 4,337,771 | 7/1982 | Pieniak et al. . |

FOREIGN PATENT DOCUMENTS

| 0023804 | 2/1981 | European Pat. Off. . |
| 0091412 | 10/1983 | European Pat. Off. . |
| 0098512 | 1/1984 | European Pat. Off. . |
| 577281 | 7/1976 | Switzerland . |
| 620816 | 12/1980 | Switzerland . |
| 2011778 | 7/1979 | United Kingdom . |
| 1554865 | 10/1979 | United Kingdom . |
| 2026323 | 2/1980 | United Kingdom . |

OTHER PUBLICATIONS

Search Report of Mar. 26, 1985 in European Patent EP 84106820-Damico et al.

Primary Examiner—C. Fred Rosenbaum
Attorney, Agent, or Firm—John L. Chiatalas

[57] ABSTRACT

The invention provides a generally narrow rectangular garment having elasticized portions centered on the long edges of the rectangle. The pad is elasticized such that shrinkage of the relaxed elastic results in a pouched formation that is well suited for use in absorption of body excretions, particularly those from incontinent adults. The pad generally has an elasticized area of between about 25 to about 60 percent of the total garment length. The elasticized edge of the pad is such that shortening of the pad amounts to between about 15 and about 37 percent of the original extended length, and the width of the pad generally ranges between about 20 and 35 percent of the total pad length.

13 Claims, 4 Drawing Sheets

INCONTINENT GARMENT WITH ELASTICIZED POUCH

TECHNICAL FIELD

The invention relates to an improved disposable absorbent garment intended to be used to receive discharge from the body. It particularly relates to disposable incontinent garments for ambulatory persons and finds particular utility in the adult active ambulatory person.

BACKGROUND

Many articles utilized as incontinent products for adults and other ambulatory persons have been found unsatisfactory as they are bulky and ineffective. Many such garments were formed by folding up flat sheets into a diaper-like structure which was bulky, particularly in the crotch portion It further had a tendency to become dislodged during activity. Other diaper-like garments such as that disclosed in the Strickland et al. patent U.S. Pat. No. 4,253,461, while successful in containing discharges for incontinent persons, are bulky and expensive. They are required to be large in order to wrap around the area of the patient from the waist to below the hip, and form a tight leg seal which is generally necessary to prevent leakage when a person is lying down. However, diaper-type garments may not be desirable for the active person as they are bulky and interfere with wearing of ordinary clothes. Further, the large amount of material utilized requires these adult diaper-type garments to be somewhat expensive.

It has been proposed that smaller disposable articles be used for incontinent adults such as the article disclosed in U.S. Pat. No. 4,182,334 to Johnson, in which a specially-folded absorbent article is utilized as a containment device for discharges, particularly from adults The device could be held in place by wearing inside an undergarment or with a suspension means. A device for adult incontinence was disclosed in U.S. Pat. No. 4,315,508, to Bolick in which a suspension system was disclosed for holding pads in the perineal region in order to minimize leakage.

U.S. Pat. No. 4,337,771 to Pieniak et al. discloses a generally rectangular pad having elasticized edges. The pad may have two or four edges elasticized. The pad is designed to be worn in a diaper-like manner by wrapping around the body. Devices such as this may be bulky and uncomfortable, having a great amount of material in the crotch area. Further, they are not comfortable or suitable for active movement.

The diaper art for infants is well-developed and discloses garments that are designed to be worn in a self-supporting manner by wrapping around the waist and being fastened.

However, there remains a need for a garment that may be worn during normal activities and will be very leak-resistant. The leak-resistance is particularly desirable when the person wearing the garment is active or when the person wearing the garment sits on the garment when wet. There is particular need for a garment that is low in cost, disposable, able to be worn discreetly under ordinary clothes, and resistant to leaks when the wet garment is worn in a sitting position

DISCLOSURE OF THE INVENTION

An object of this invention is to overcome disadvantages of the prior art.

An object of this invention is to produce an incontinent garment that will be effective but not visable under street clothes.

A further object of this invention is to produce a garment that will resist leaks during a person's activities.

It is another object of this invention to produce a garment that will protect from leakage when it is sat upon when wet.

Another object of this invention is to produce a low-cost incontinent garment.

An additional object of this invention is to produce an incontinent garment that will allow comfortable wear.

It is another additional object of this invention to produce an incontinent-care garment that will allow active movement while being worn.

These and other objects of the invention are generally accomplished by providing a generally narrow rectangular garment having elasticized edges with the elastic generally centered on the long edges of the rectangle. The pad of the invention generally has a width that is only between about 20 and about 35 percent of the total extended pad length. The pad further has an elasticized area of between about 25 and about 60 percent of the total garment length. The elasticized edge of the pad is such that the shortening of the pad amounts to between about 15 and about 37 percent of the original extended length. In a preferred embodiment for adults, the width is about 28 percent of the length and the length of the elasticized area to the overall pad length, is between about 40 and about 56 percent. The pad of the invention may be held in place by support devices or be worn inside an undergarment.

MODE FOR CARRYING OUT THE INVENTION

The invention has numerous advantages over the prior art. The device of the invention is not bulky and allows activities of ambulatory people wearing the device without embarrassment. Further the device has a very low tendency to leak. The device further is low in cost as it is formed of a rectangular shape thereby allowing full use of raw materials. Complicated shapes requiring leg cutouts or other intricate shapes require wasting of material in making these cutouts. The device is easy to make as it does not require folding, which contributes to low-cost production. The device is more comfortable as it produces a pouch effect such that the material contained in the is less likely to be in contact with the perineal region. Further, the organs of the perineal area are not rigidly confined thereby causing discomfort. A further advantage, particularly with the baffled garment, is that the garment is less likely to leak when sat upon when wet than other garments. The garment's elastic portion at the edges of the perineal region further makes the wearer feel more secure and less concerned about staining or leaking. These and other advantages will become clear from the detailed description that is given below.

Figure 1:
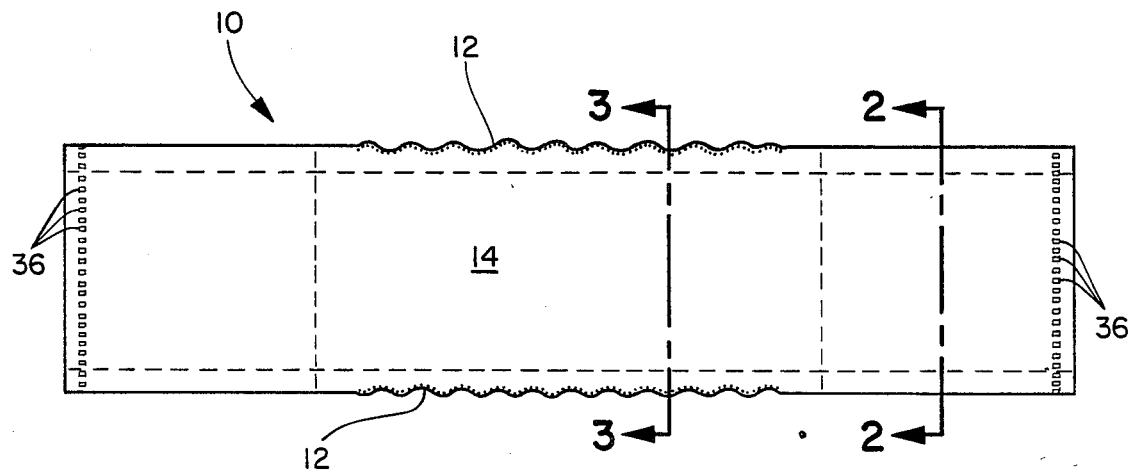
FIG. 1 is a plan view of a garment of the invention in extended condition with the body-contacting portion facing the viewer.

The pouch-pad garment indicated as 10 in FIG. 1 is shown in extended condition. By this it is meant that the pad elastic is fully extended so the pad is flat. The pad 10 as seen from top view comprises a generally rectangular member having a shirred edge 12, where the elastic is attached to the inner portion of the polymer sheet at the edge of the garment and a body facing pervious liner 14 overlaying the pad and impervious back sheet member. As indicated in the cross-section view, FIG. 2, taken at line 2—2 of FIG. 1, the pad comprises the body facing member 14 of pervious material, inner lower pad member 16, and impervious polymer member 18, which is wrapped around pad member 16 and adhered to facing member 14 at 22 and 24. This structure provides that the body facing porous sheet covers the impervious member at the edges. The overlap of the backing member 18 at 22 and 24 creates a baffle area of impervious sheet 26 and 28 that aids in containment of bodily discharges when the device is in use. The center portion of the pad 10, as illustrated in FIG. 3, contains an additional layer of absorbent material 30, and further has elastic members 32 and 34 extending along the longitudinal edges of the rectangular pad. While the devices are shown with two layers of padding it is, of course, within the invention to utilize any number of desired layers or to use unitary pads that are formed with a thicker portion in the middle. However, for simplicity of formation, the use of a thickened center portion formed by additional layers of absorbent padding is simple and does not result in waste of material.

Figure 4:
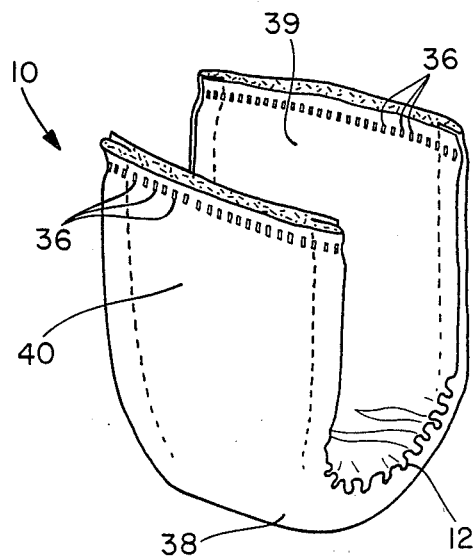
FIG. 4 is a prospective view of garment of the invention when in a position such as it assumes during use.

FIG. 4 is a view of the pouch pad of the invention 10 in a relaxed condition and generally in the form assumed when it is worn. The spots 36 are places where the impervious back sheet pad, and body-side face sheet were ultrasonically sealed together. The device has a pronounced pouch 38. The elasticized area 12 has assumed a bunched shape and is well raised above the bottom of the pouch 38. The non-elasticized areas 39 and 40 extend up in front of and behind the person wearing the garment, provide extra absorbent material that may be needed when sitting and also may be utilized to position fasteners to keep the garment in place.

Figure 5:
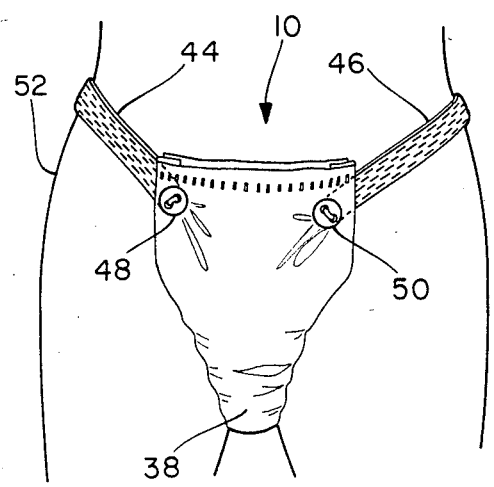
FIG. 5 illustrates the garment of the invention when worn with a suspension system.

FIG. 5 represents a garment in accordance with the invention held in place by the suspension system disclosed in U.S. Pat. No. 4,315,508, in which elastic members 44 and 46 extend up over the hips of the wearer and provide an upward force onto the garment 10. The straps 44 and 46 are terminated by button-like devices 48 and 50 that extend through holes in the garment 10. It is also possible that the garment may be held in place by being worn inside a tight-fitting undergarment.

Figure 6:
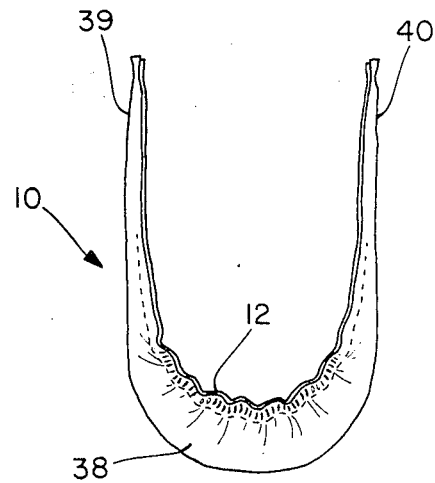
FIG. 6 is a plan view of the garment of the invention viewed when the garment is positioned in a manner similar to the shape when in use.

FIG. 6 is a sideview of the garment 10 in which the pouch-like effect of the garment is clearly illustrated. In the invention garment the depth between the elastic edge and the bottom of the garment in the center portion may be about 2 inches in a garment of overall size of 25"×7".

Figure 7:
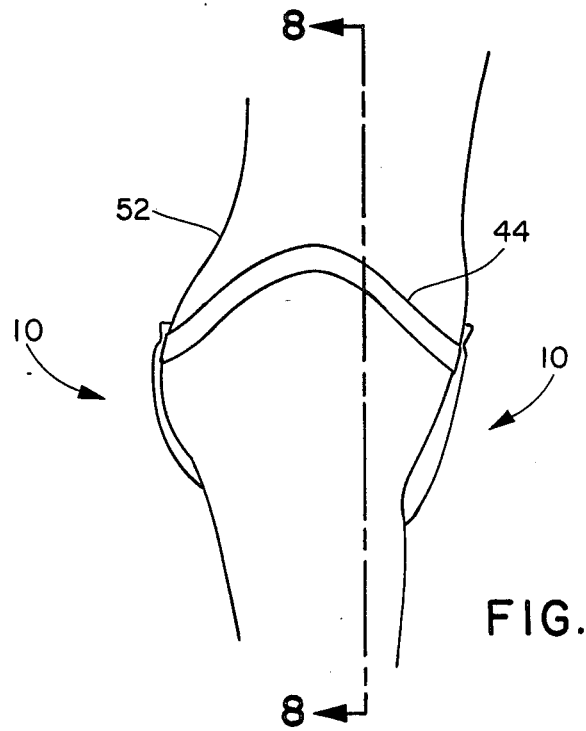
FIG. 7 is a side plan view of a person wearing the garment of the invention.
Figure 8:
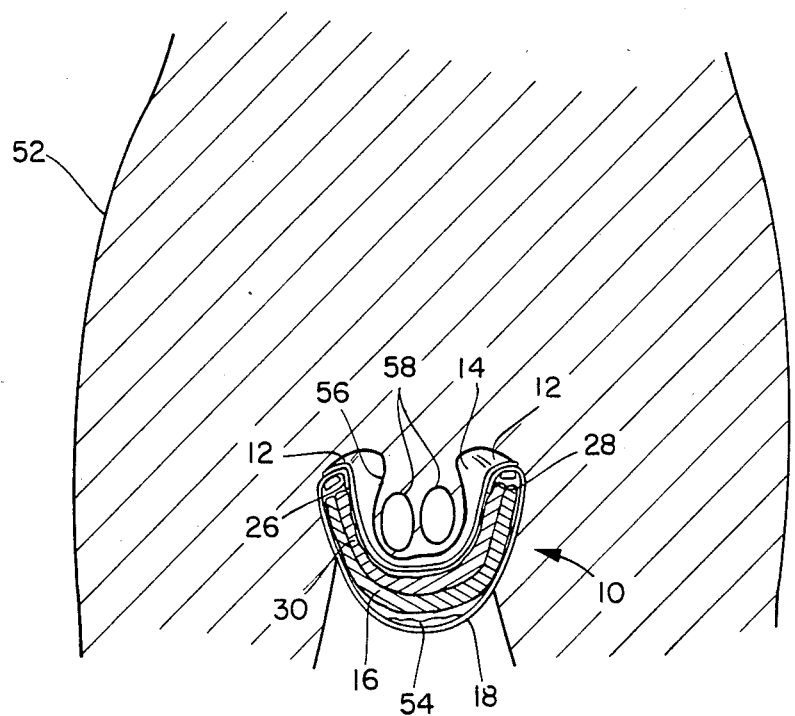
FIG. 8 is a cross-sectional view of the garment in use taken along line 8—8 of FIG. 7.

As illustrated in FIGS. 7 and 8, the garment of the invention 10 is worn by a person 52. FIG. 8 is a cross-sectional view on line 8—8 of FIG. 7. The garment of the invention 10 is illustrated and the benefits of the pouch formed in the invention are illustrated. The device with the impervious outer shield 18 and the swollen absorbent materials 16 and 30 has retained urine in the absorbent and also some urine 54 which has pooled. As can be seen from the illustration, the baffles 26 and 28 will prevent the overflow of urine 54 during activities. Further, the baffles 26 and 28 will direct the flow of urine along the edge of the pad rather than over the edge when pad is sat upon or compressed by movement. The elastic edges 12 hold the edges higher than the lower center portion when it is worn and further provide a pouching effect for comfortable fit around the scrotum 56 and testicles 58 of the wearer 52. Further, the elastic members holding the device in place without discomfort provide a feeling of security to the wearer that leakage will not leak during activities. While shown with a male wearer, the device also, of course, is suitable for women.

Figure 9:
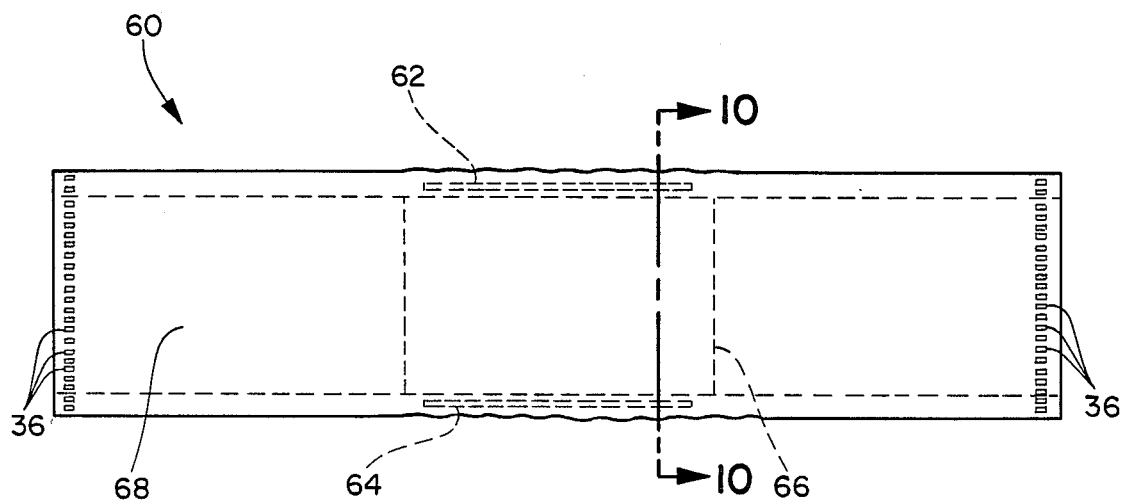
FIG. 9 is a plan view of an alternative garment of the invention without the baffle feature.
Figure 10:
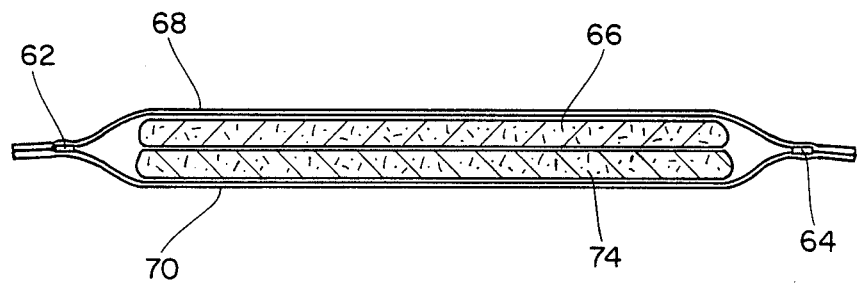
FIG. 10 is a sectional view on line 10—10 of FIG. 9.

FIGS. 9 and 10 illustrate a less preferred embodiment of the invention in which baffles are not present, indicated generally as 60. In this embodiment the baffle is not present. The pervious body side liner 68 and the impervious backing sheet 70 are joined at the sides, and the elastics 62 and 64 are located between the pervious liner 68 and backing sheet 70. The device is illustrated with two absorbent filler sheets (66 and 74) similar to that illustrated in the preferred embodiment. However, as before stated, the number filler sheets and their thickness may be varied although the device generally should have more absorbence in the pouch portion.

It is theorized that the device of the invention is particularly advantageous over prior art devices in that the amount of stress that is utilized in the elastic is very high thereby shortening the edges of the elasticized portion a great deal, causing the pouched effect. It is theorized that this high degree of contraction is suitable for the invention garment in that no leg seals are being formed as in diaper-type garments. A high degree of contraction in a garment forming leg seals will cause red marks and difficulty in circulation whereas in a device such as the instant invention the elastic acts primarily to shape the garment and the force of the elastic is not applied directly to the body or around the legs of the person wearing the garment. However, the elastic does contact the body of the wearer and may exert slight pressure, contributing to a feeling of security in wearing the garment.

It has been found that the pad of the invention has specific dimensions and properties which are believed interrelated to result in the particularly desirable garment of the invention. The pad of the invention is generally narrower than previous garments utilized for absorption of body excretions. The width of the pad is generally found to be between about 20-35 percent of the extended pad length in order to have good wearing characteristics and desired pouch shape in addition to providing enough absorbent material. It has been found that a particularly preferred article for use in adult incontinence protection has a width of about 28 percent of the length dimension for comfortable wearing and large capacity for holding of excretions. Another dimension which has been found to be of importance with the invention is the relationship of length of the elasticized area to the total pad length. The elasticized material is located on the long side of the rectangular pad and is generally centered on the long side so as to leave equal non-elasticized portions at each end. It has been found suitable that the length of extended elasticized material be between about 25 and 60 percent of the total pad length in order to create the desired pouch effect. The particularly preferred form for use in adult incontinent care has a length of the elasticized area of between about 40–56 percent of the total pad length for good pouch formation and comfort to the wearer. A property that is also important in the instant invention is the amount of foreshortening of the pad caused by the elastic. As stated above, the elastic in the instant pad is highly stretched when attached and therefore a relatively great amount of shortening takes place. It is, of course, possible that thicker elastic stretched by a smaller amount could cause the same amount of foreshortening and the type of elastic is not believed critical. The important feature is the amount of foreshortening which will cause the desired pouch effect. The relaxed pad is generally measured by placing the pad with the body-side portion facing upward and gently flattening it by hand prior to measurement. The amount of pressure required for flattening is no more than that applied by a two-to-three-pound book of $9\frac{1}{2}'' \times 11''$ size laying on the pad. The amount of foreshortening of the entire pad length caused by the shrinkage of the elastic is suitably between about 15–37 percent of the overall extended pad length. The preferred amount is between about 20–32 percent of extended pad length for creation of a good pouch that is readily moldable to body contours.

The pads of the invention may be made any desirable size as long as the relationship of the dimensions is within the above-listed parameters. However, it may be stated that for a typical adult incontinent garment the width is about 7 inches and the overall extended pad length is about 25 inches. However, generally the pad size ranges for extended adult garments would be considered in the range of between about 18 and about 29 inches for length and about 5 and about 8 inches for width. It is, of course, possible that when the garments are used for bodily excretion not related to incontinence, i.e., wounds of the knee or head, that smaller dimensions would be used. For instance, a pad suitable for use with an elbow may be about 5 inches × 20 inches. Head bandage garments are of similar size to those for incontinent care garments or may be slightly smaller such as 6 inches by 27 inches. Further, it is possible that the overall length could be extended by nonused material to a longer length for other purposes such as to fasten attachment means.

The impervious backing sheet of the invention may be any suitable flexible impervious film. Typical of such materials are films of polyvinyl chloride, polyesters, and other polymer materials. Preferred materials are the linear polyolefin films such as polyethylene and polypropylene as they are low cost and quiet. The backing sheet may be of laminated construction as long as one of the laminated sheets is impervious.

The body-side liner material may be any porous material that is generally nonwetting and porous to fluids. Typical such materials are nonwoven webs of cellulose materials, nonwoven webs of synthetic fibers such as polyester, perforated polymer films, and porous woven materials. A preferred material is spunbonded polypropylene which is a material formed by meltblowing of extruded polypropylene The material is strong and does not greatly deteriorate in strength when wet. While the body-side liner is illustrated as a rectangular piece of the same size as the garment, it may be that in some manufacturing techniques it would be desired to wrap the pervious material entirely around the garment. In that case only the portion over the absorbent would be necessary.

The absorbent material forming the absorbent portion of the device of the invention may be any of many well-known absorbent materials such as cellulose fibers ordinarily referred to as fluff or mixtures of cellulose fibers and meltblown artificial fibers. Further, it is within the invention to utilize other absorbent materials such as superabsorbents or artificial sponge material. The preferred material has been found to be blends of polypropylene and cellulose fibers that are formed by blowing cellulose fibers into polypropylene fiber during formation such as those formed by the process of U.S. Pat. No. 4,100,324. It is further possible to use combinations of batts of different material and to use any desired number of layers. Generally the device would be formed with a thicker absorbent filling in the pouch portion.

The device of the invention may be held in place by numerous means. As illustrated in the drawings, the device is shown held up with a suspension elastic that is terminated by buttons which fit through holes in the garment. Other suspension devices may be utilized such as elastics with clips which fasten onto the device or adhesive connections or VELCRO fasteners. Further, rather than being held in suspension, the device may be utilized with tight-fitting undergarments. These garments may be either specially designed garments or the pouch pad may be worn inside ordinary underwear of the brief style.

The device of the invention is of particular advantage in that it is not greatly noticeable under ordinary clothing. It is noted that the device ordinarily will not extend above the navel of the wearer in the front and also reaches to a similar low level in the back. Further, as was illustrated in the drawings, the device generally has less padding in what will be the upper portion when worn. The absorbent in the upper areas generally would be utilized when the person wearing the garment sat down and fluid then would be forced into the upper portions.

Figure 2:
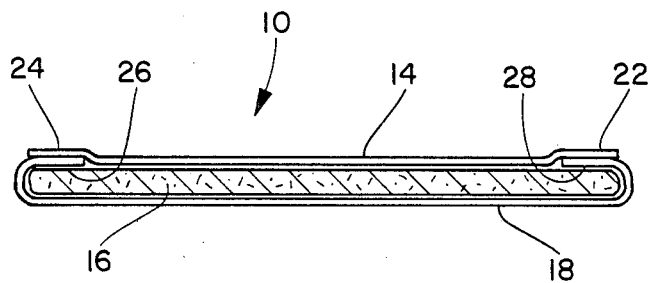
FIG. 2 is a cross-section view of the invention garment taken on section line 2—2 of FIG. 1.
Figure 3:
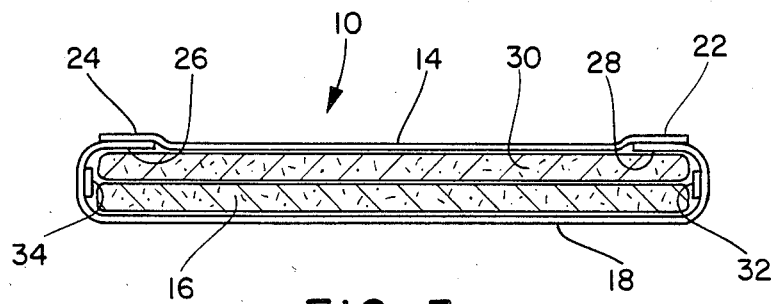
FIG. 3 is a cross-sectional view of the invention garment taken on line 3—3 of FIG. 1.

While the invention is illustrated in FIGS. 1 through 3 with the baffles (26 and 28) located beneath the pervious body-side lining 14, it would also be within the invention to place the baffles on the outer surface. This would have the disadvantage that the plastic would be in contact with the skin such that it would be likely to be less comfortable. However, there might be somewhat less chance of wicking of the fluids from the garment as the pervious material does not extend to the edge. The baffle is effective whether it is below or above the pervious liner.

The following example is intended to be illustrative of a method of forming a pouch pad in accordance with the invention. This is a laboratory technique of making the device and, of course, would be automated in commercial production. However, it will be clear from the example below, that the device is easily constructed without intricate cutting or folding required.

EXAMPLE

A piece of polypropylene sheeting of about 0.7 mils thickness is cut to a size of 9 inches by 27 inches. This sheet is taped to a laboratory table in an extended flat position. An absorbent member is cut to a size of about 7 inches by 14 inches and centered onto the polypropylene sheet. Another sheet of absorbent material is cut to a size of about 7 inches by 25 inches and this is also centered onto the polypropylene sheet to leave about an inch on each longitudinal edge and about an inch on each of the shorter edges exposed. The absorbent sheet was a sheet formed of a combination of meltblown polypropylene and cellulose fibers. Each pad was about 3/16 of an inch thick when dry. Next two-sided tape of about 1 inch width was placed on the exposed longitudinal edges. Next the elastic pieces for the edge were cut. These were natural rubber about ¼ inch wide and about 7 mil thickness. In a relaxed condition, these pieces were 4½ inches long. The pieces were stretched 14 inches and stuck to the tape immediately adjacent the absorbent material and centered in the longitudinal portions. The exposed longitudinal edges having two-sided tape on them are then folded over and adhered to the pad. This has the effect of forming the baffle and also concealing the tape from contact with the skin in the finished article. Next a ½ inch wide portion of two-sided tape was applied to the marginal longitudinal edge of the pad. This tape is therefore located on the outside of the folded baffle. Next the body-side liner of spunbonded polyester was cut to a size of 7 inches by 25 inches and laid on top of the pad and sealed at the edges to the tape. The pad was then cut lose from the laboratory table and the end portions were sealed with an ultrasonic gun. The excess polypropylene sheet on the end portions was cut off such that the backing member and the pad and body-side material were the same length.

After being cut free of the laboratory table the pad was of course shortened by the elastic which attempted to return to its original length. The length of the pad after shortening was about 18½ inches. This length is measured after laying the pad flat and weighting the elastic portion with a book of about 2½ pounds weight and about 11 inches long. This shortening of the elastic had the effect of creating the pouch and forming the pouch pad of the invention. Pads formed such as in this example were tested on several ambulatory people having incontinence problems and found to have a very low level of leakage. Further, the pouch pad was found to be comfortable to wear, giving feeling of security and was particularly resistant to leaks when it was sat upon when wet.

While the invention has been discussed primarily with respect to the use of the pad of the invention as an incontinent garment, the pouch pad of the invention has other uses, particularly in the area of use as bandaging or as a garment to prevent chaffing and irritation of the skin in areas of abrasion. When used in this manner, it may prevent bed sores or blistering. For instance, the pad when made in the proper size finds utilization as a bandage for a knee wound. When used in this manner, a two-sided tape with cover means may be placed on to the end of the pad so that after it is wrapped around the knee it may be sealed. Alternatively, the device may be taped in place. Also, the pad of the invention may be used as a prophylactic measure to prevent bed sores. Such a use would be achieved when properly-sized garments are wrapped around the bodily protrusions such as the heels, elbows, and knees. The device further finds utility as a bandage device for head wounds as the pouch shape adapts itself to being held in place upon the head.

These other uses of the garment may find particular utility in the nursing home environment as it would make the garment a multi-purpose unit that could be used in the same size for head bandages and incontinent care. Further, sizes suitable for wrapping knees also would be suitable for use in incontinent care of incontinent children or small adults. This would be a savings in the hospital and nursing home environment as fewer bandaging and care devices would be necessary.

The above description is intended to be descriptive and not exhaustive of the possibilities of the invention. For instance, while the invention is disclosed with utilization of natural rubber elastics, it is possible that the device could be formed with elastics of self-adhesive rubbers or other types of artificial rubber Further, while disclosed with a plain polymer sheet surface, it also would be within the invention to provide the article with a decorated finish or bond the polymer covering material to a fabric surface which would provide better feel to the patient and quiet the crinkling of some polymer materials. It is noted that generally polypropylene films are relatively quiet when worn at body temperatures, but at lower temperatures there is more tendency to crinkle. Addition of a fibrous or cloth covering to the polypropylene would make the garment more esthetically pleasing prior to use.

We claim:

1. A disposable, absorbent pouched pad comprising a generally rectangular impervious backsheet, a generally rectangular pervious body-side liner joined to said backsheet at their edges, an absorbent liner between the topsheet and the backsheet, elastic portions generally centered at the peripheral portions of the long edges of said generally rectangular liner and back sheet, wherein said pad width is between about 20 percent and about 35 percent of the extended total pad length, the length of said elasticized area when the elastic is in extended condition is between about 25 percent and about 60 percent of the total pad length and the shortening of the total pad length when the elastic relaxes is between about 15 and about 37 percent of the extended length.

2. The pad of claim 1 wherein said impervious backsheet is folded so as to overlap part of the pad surface.

3. The pad of claim 1 wherein said shortening of the pad when the elastic relaxes is between about 20 and 32 percent.

4. The pad of claim 1 wherein said length of elasticized area to pad length is between about 40 and about 56 percent of total pad length.

5. The pad of claim 1 wherein said elasticized portion has a width of about 28 percent of the length of the extended elasticized portion.

6. The pad of claim 2 wherein the impervious portion overlapping said pad is covered by said liner.

7. The pad of claim 1 wherein said elasticized portions when contracted form a pouch.

8. The pad of claim I wherein the depth of the pouch is about 2 inches below the elastic sides.

9. A method of incontinence protection for ambulatory people comprising providing a pouched absorbent pad, said pad comprising a substantially rectangular impervious backsheet, a generally rectangular pervious body-side liner joined to said backsheet at their edges, an absorbent layer between said topsheet and said backsheet, the long edge portions of said impervious backsheet folded so as to cover a portion of the edge of the absorbent pad, and elastic portions generally centered in the peripheral portions of the long edges of said pad wherein said elasticized portion of the pad has a width of between about 20 percent to about 35 percent of the total length of said pad, the length of said elasticized area when the elastic is in the extended condition is between about 40 percent and about 56 percent of the total pad length, and the shortening of the pad when the elastic relaxes is between about 20 and about 32 percent of the extended length, holding said pouched pad in the perineal region of an ambulatory person with the non-elasticized end portions extending upward behind and in front of the person while the pouched portion is in the perineal region, whereby said folded-over portions of the impervious backsheet form said baffles to contain urine or other liquid waste.

10. The method of claim 9 wherein said baffles direct fluid flow along the edges of said garment.

11. The method of claim 9 wherein said pad is held in place by elastic supports.

12. The method of claim 9 wherein said pad is held in place by an undergarment.

13. The method of claim 9 wherein the pouch has a depth of about two inches below the side elastics.

* * * * *